(12) United States Patent
Matsui et al.

(10) Patent No.: US 7,756,564 B2
(45) Date of Patent: Jul. 13, 2010

(54) APPARATUS FOR MEASURING THE NEURO-MAGNETIC FIELD FROM A HUMAN BRAIN AND METHOD FOR OPERATING THE SAME

(75) Inventors: Toshiaki Matsui, Koganei (JP); Hiroshi Ohta, Koganei (JP)

(73) Assignee: National Institute of Information and Communications Technology, Tokyo (JP)

( * ) Notice: Subject to any disclaimer, the term of this patent is extended or adjusted under 35 U.S.C. 154(b) by 116 days.

(21) Appl. No.: 11/192,514

(22) Filed: Jul. 29, 2005

(65) Prior Publication Data

US 2005/0272996 A1 Dec. 8, 2005

Related U.S. Application Data

(63) Continuation of application No. PCT/JP03/000836, filed on Jan. 29, 2003.

(51) Int. Cl.
*A61B 5/05* (2006.01)

(52) U.S. Cl. .............. 600/409; 600/407; 600/408; 324/301; 505/162

(58) Field of Classification Search ......... 600/407–409; 324/301, 302, 244–263; 505/162
See application file for complete search history.

(56) References Cited

U.S. PATENT DOCUMENTS

| 5,081,071 | A * | 1/1992 | Hirschkoff | 505/162 |
| 5,406,847 | A * | 4/1995 | Rowe et al. | 73/504.02 |
| 5,418,512 | A * | 5/1995 | Ohta et al. | 505/162 |
| 6,486,393 | B1 * | 11/2002 | Matsuba et al. | 174/391 |
| 6,512,368 | B2 * | 1/2003 | Tanaka et al. | 324/248 |
| 7,130,675 | B2 * | 10/2006 | Ewing et al. | 600/409 |
| 2002/0050815 | A1 * | 5/2002 | Suzuki et al. | 324/248 |
| 2004/0002645 | A1 * | 1/2004 | Ewing et al. | 600/409 |
| 2004/0049108 | A1 * | 3/2004 | Ardenkjaer-Larsen et al. | 600/412 |
| 2004/0106863 | A1 * | 6/2004 | Seki et al. | 600/409 |

(Continued)

FOREIGN PATENT DOCUMENTS

JP 05-212008 8/1993

(Continued)

OTHER PUBLICATIONS

Hiroshi Ohta, "Ceramics 35" (2000), No. 2, "Whole-Head-Type SQUID System in a Superconducting Magnetic Shield of High Critical-Temperature Superconductor."

(Continued)

*Primary Examiner*—Brian Casler
*Assistant Examiner*—Nasir Shahrestani
(74) *Attorney, Agent, or Firm*—Blakely, Sokoloff, Taylor & Zafman LLP

(57) ABSTRACT

The present invention provides a low-noise MEG apparatus of high sensitivity. A MEG apparatus using a magnetic shield of high critical temperature superconductor is set on the floor of a building via mechanical vibration suppressor supports to prevent appearance of noise signals. Also, the apparatus is equipped with means for preventing any relative displacement between the SQUID magnetic sensors and the magnetic shield of high critical temperature superconductor, thereby not letting an inevitable mechanical vibration of least strength produce any variable components of the trapped static magnetic field, which the SQUID magnetic sensors could be sensitive to.

3 Claims, 8 Drawing Sheets

U.S. PATENT DOCUMENTS

2004/0254443 A1* 12/2004 Gott et al. .................. 600/409
2005/0206377 A1* 9/2005 Romalis et al. ............. 324/301
2008/0108504 A1 5/2008 Matsui et al.

FOREIGN PATENT DOCUMENTS

| JP | 05-264693 | 10/1993 |
| --- | --- | --- |
| JP | 07-294613 | 11/1995 |
| JP | 10-313135 | 11/1998 |
| JP | 2001-178695 | 7/2001 |
| JP | 2002-315729 | 10/2002 |
| JP | 2002-372098 | 12/2002 |
| JP | 2003-010142 | 1/2003 |
| WO | WO 2006/067828 A1 | 6/2006 |

OTHER PUBLICATIONS

Hiroshi Ohta, et al., "Nanometer SNS Junctions and Their Application to SQUIDs", Physica C 352 (2001), pp. 186-190.

H. Ohta, et al., "A 64-Channel Whole-Head SQUID System in a Superconducting Magnetic Shield," Supercond. Sci. Technol. 12 (1999), pp. 72-765, printed in the U.K.

International Search Report for PCT Counterpart Application No. PCT/JP03/00836, 3 pgs. with English translation of the International Search Report for PCT Counterpart Application No. PCT/JP03/00836, 4 pgs. (May 20, 2003).

Patent Cooperation Treaty's Written Opinion for International application No. PCT/JP03/00836, 6 pgs. with English translation of the Patent Cooperation Treaty's Written Opinion for International application No. PCT/JP03/00836, 5 pgs. (Dec. 2, 2003).

PCT Notification of Transmittal of International Preliminary Examination Report for PCT Counterpart Application No. PCT/JP03/00836, 6 pgs. with English translation of the PCT Notification of Transmittal of International Preliminary Examination Report for PCT Counterpart Application No. PCT/JP03/00836, 5 pgs. (Mar. 30, 2004).

* cited by examiner

Prior Art

Prior Art

APPARATUS FOR MEASURING THE NEURO-MAGNETIC FIELD FROM A HUMAN BRAIN AND METHOD FOR OPERATING THE SAME

CROSS-REFERENCE TO RELATED APPLICATIONS

This is a continuation of prior PCT Patent Application No. PCT/JP2003/000836, filed on Jan. 29, 2003.

TECHNICAL FIELD

The present invention relates to an apparatus for measuring the neuro-magnetic field generated around a human head by the current flowing in the nerves of the brain when it works, approximately one hundred million times as small as the magnetic field of the earth, and a method for operating the same.

A SQUID (Superconducting Quantum Interference Device) immersed in a liquid helium bath can work as a sensor for magnetic fields at a very low temperature to detect such a weak magnetic field. Thus, the observation of the dynamics of the neural network of the brain is enabled. So, diagnosis can be made of the function of the brain (such as memory, learning, attention and other mental acts) and of some brain disorders (attention deficit hyperactivity disorder, learning disabilities, autism or schizophrenia).

BACKGROUND ART

The present inventor developed a low temperature type system of neuro-magnetic field sensors in which a SQUID can be used while being immersed in a liquid helium bath. The instrument has been practically used.

Referring to FIG. 5, a conventional SQUID (MagnetoEncephaloGraphy or MEG) apparatus 1 comprises a vacuum structure 11 of hollow cylinder for thermal insulation, a closed-cycle Helium refrigerator 12, a liquid-Helium dewar 13, and a top cover 14. The vacuum structure 11 for thermal insulation of a hollow cylinder contains two cylinders—a first, inner cylinder 111 of high critical temperature superconductor material and a second, outer cylinder 112 of high-permeability magnetic material both arranged coaxially in its annular space. The closed-cycle Helium refrigerator 12 circulates a cooled Helium gas to cool the inner cylinder of high critical temperature superconductor material in the vacuum structure 11 for thermal insulation. The liquid-Helium dewar 13 is arranged coaxial to the vacuum structure 11 for thermal insulation. The top cover 14 is of double structure of a metal of electrically conductive material (taking part of shielding electromagnetic wave) and a magnetic material (taking part of shielding magnetic field), and is adapted to fit the top of the vacuum structure 11 for thermal insulation.

The lower part of the liquid-Helium dewar 13 defines a head accommodating area 131 to accommodate the head of a patient under inspection. The liquid-Helium dewar 13 has a plurality of SQUID magnetic sensors 15 therein. The SQUID magnetic sensors 15 are fixedly arranged on a support block 20 around the head accommodating area 131. The liquid-Helium dewar 13 is filled with liquid Helium of cryogenic temperature.

The vacuum structure 11 for thermal insulation is supported by the horizontal shafts on the four legs. It has a non-magnetic chair 17 placed in its lower opening. The top cover 14 of magnetic material is put on the top of the vacuum structure 11 for thermal insulation, effectively preventing invasion both of the geomagnetism and the electromagnetic wave from the top.

The conventional MEG apparatus is described in the following documents: (Patent Document)

Patent Application Public Disclosure No. 10-313135; and (Non-Patent Document)

"Whole-Head-Type SQUID System in a Superconducting Magnetic Shield of High Critical-Temperature Superconductor", by Hiroshi Ohta, "Ceramics 35" (2000), No. 2. Extra Edition. Titled "Brain and Ceramics; Ceramics Useful in Illustrating the Functions of the Brain, Making the Diagnosis of the Brain Disorders and Carrying out Required Treatments", and "Nanometer SNS Junctions and Their Application to SQUIDs", by Hiroshi Ohta et al, "PHISICA C" 352 (2001), p.p. 186-190

Conventionally it is used to be necessary that the SQUID (MEG) system be completely isolated from the floor of a building to avoid mechanical vibrations. The complete isolation of the SQUID (MagnetoEncephaloGraphy or MEG) system from any mechanical vibrations requires rigid floors of the building usually. Also, an optimum installation site should be chosen to avoid mechanical vibrations from the surroundings such as traffic of automobiles; if not, the MEG system installed in the existing building could not be of practical use. When a building which a MEG system is to be installed in is constructed, the solid underground base of the building needs to be rigid and strong enough to shut off any mechanical vibrations from the surroundings, and accordingly the required foundation work takes much money to build.

Referring to FIG. 6, a MEG system was installed in an existing building with a rigid foundation, and the signals from the typical fifteen SQUID magnetic sensors 15 among 64 sensors of the system were plotted with time (abscissa). As seen from these records, most of 15 channels have significantly large noise signals while no patient was under inspection. At the outset we were not able to identify sources of such noise signals, and it took some time before we recognized that the source of such significant noise signals is constant, ceaseless vibrations of minimum amplitude from the floor.

FIGS. 7 and 8 show the vacuum structure 11 for thermal insulation and the liquid-Helium dewar 13 at an enlarged scale. Referring to these drawings, assuming that the first cylinder 111 of the high critical temperature superconductor material (bismuth-strontium-calcium-copper-oxides: BSCCO) is cooled down to around the liquid nitrogen temperature (below Tc=103 K), invasion of magnetic flux in the inner space of the vacuum structure 11 for thermal insulation would be supposed to be completely prevented. Before the first cylinder 111 is cooled down, however, the geomagnetic field has already invaded into the inner space of the vacuum structure 11 for thermal insulation, and then, the geomagnetic field is pin-fastened to the first cylinder 111 in the state of being trapped. In this position if the liquid-Helium dewar 13 moves relative to the first cylinder 111 longitudinally or up and down (see FIG. 7) or laterally or from side to side (see FIG. 8), the magnetic component of the trapped static magnetic field across the SQUID sensors 15 will vary (see FIGS. 7 and 8; magnetic fluxes and sensors after displacement being shown by broken lines), thereby causing noise signals to appear.

One object of the present invention is to provide a noise-free MEG apparatus of high-sensitivity. Another object of the present invention is to provide a method of putting such MEG apparatus in operation.

DISCLOSURE OF THE INVENTION

To attain this object, a noise-free MEG system of high-sensitivity according to the present invention is designed to completely isolate the apparatus from the floor on which it is placed in respect of mechanical vibrations, thereby assuring that the apparatus be guaranteed to be free of excursion to the disturbed positions as described with reference to FIGS. 7 and 8. Specifically, the MEG apparatus of FIG. 5 is modified to support the vacuum structure for thermal insulation on the floor via a mechanical vibration-suppressor support, thereby preventing transmission of any mechanical vibrations to the vacuum structure for thermal insulation. According to the present invention the mechanical vibration-suppressor support comprises means for absorbing any mechanical vibrations from the floor and anti-mechanical vibration mechanism sensitive to any mechanical vibrations from the floor to cancel and nullify the adverse effect on the vacuum structure for thermal insulation by means of feed-back control.

Also, to attain the above object the magnetic sensors are fastened so as to eliminate any relative displacement between the magnetic sensors and the first cylinder of critical temperature superconductor material, thereby assuring that the magnetic sensors be prevented from traversing across the stationary magnetic fluxes trapped in the inner space of the vacuum structure for thermal insulation (see FIGS. 7 and 8). Thus, the magnetic component traversing each magnetic sensor cannot vary relative to the sensor, and therefore no noise signals can appear. FIG. 7 shows the longitudinal displacement of the liquid-Helium dewar in an exaggerated way (dot-and-dash lines). Obviously the liquid-Helium dewar and the vacuum structure for thermal insulation (and hence, the first cylinder of high critical temperature superconductor material) move up and down as a whole, thereby keeping the positional relationship between the magnetic sensors and the trapped static field unchanged. As seen in the drawing, the relative position of magnetic flux and sensors for the post-movement (dot-and-dash lines) is the same as that for the pre-movement (broken lines); the magnetic flux component traversing the sensors do not change. In this particular embodiment the fastening means used for that purpose comprises a first pillow structure to fill the gap between the inner wall of the vacuum structure for thermal insulation and the outer wall of the liquid-Helium dewar. In case that a superconducting canopy is placed above the magnetic sensors in the liquid-Helium dewar to prevent invasion of the magnetic field from the above, a second pillow structure is used to fill the gap between the superconducting canopy and the inner wall of the liquid-Helium dewar. The second pillow is placed next to the lowest end of the liquid-Helium dewar, where the mechanical vibration amplitude would be of maximum value.

The MEG apparatus equipped with the fastening means just described and the mechanical vibration suppressor support above described allows the magnetic sensors and the vacuum structure for thermal insulation to move as a whole in response to any mechanical vibration force from the floor even though it cannot be suppressed by the mechanical vibration suppressor support, thereby keeping the trapped magnetic field stationary with respect to the magnetic sensors. Thus, no noise signals can appear in the magnetic sensors.

The method of putting the MEG apparatus in operation according to the present invention comprises the steps of:

closing both the top and the bottom openings of the vacuum structure of hollow cylinder for thermal insulation with each magnetic member (thereby preventing invasion of the geomagnetism into the inner space of the vacuum structure for thermal insulation); cooling the first cylinder down to around the liquid nitrogen temperature (thereby preventing trapping of the geomagnetism by the high critical temperature superconductor); filling the liquid-Helium dewar with liquid helium or cooling the liquid-Helium dewar by means of thermal conduction to the cryogenic temperature (thereby preventing trapping of the geomagnetism by SQUID magnetic sensors, and hence preventing the adverse effect on the magnetic sensors for their malfunction); and measuring the neuro-magnetic field by the SQUID magnetic sensors.

PREFERRED EMBODIMENTS OF THE PRESENT INVENTION

Figure 1:
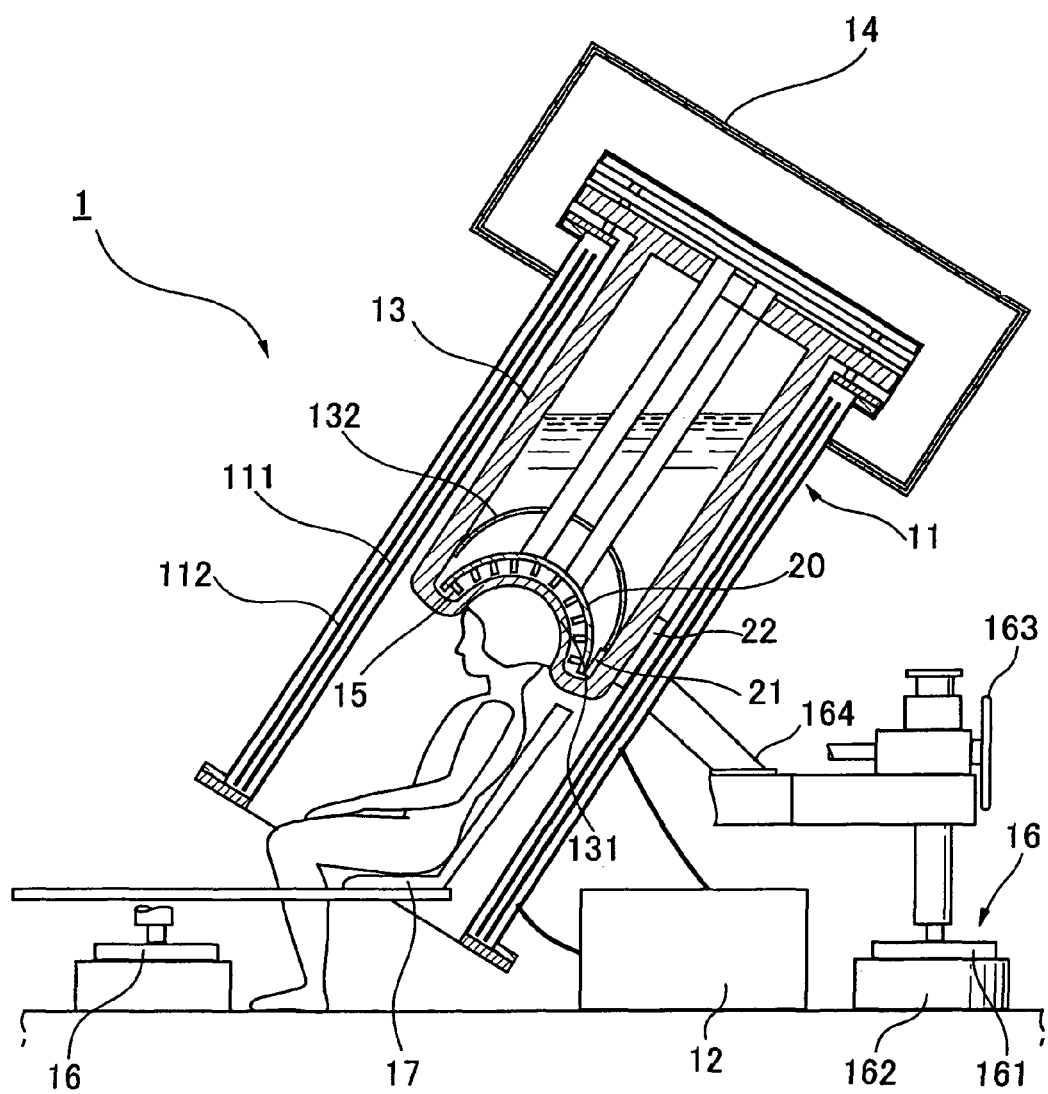
FIG. 1 illustrates diagrammatically a MEG apparatus according to one embodiment of the present invention.
Figure 5:
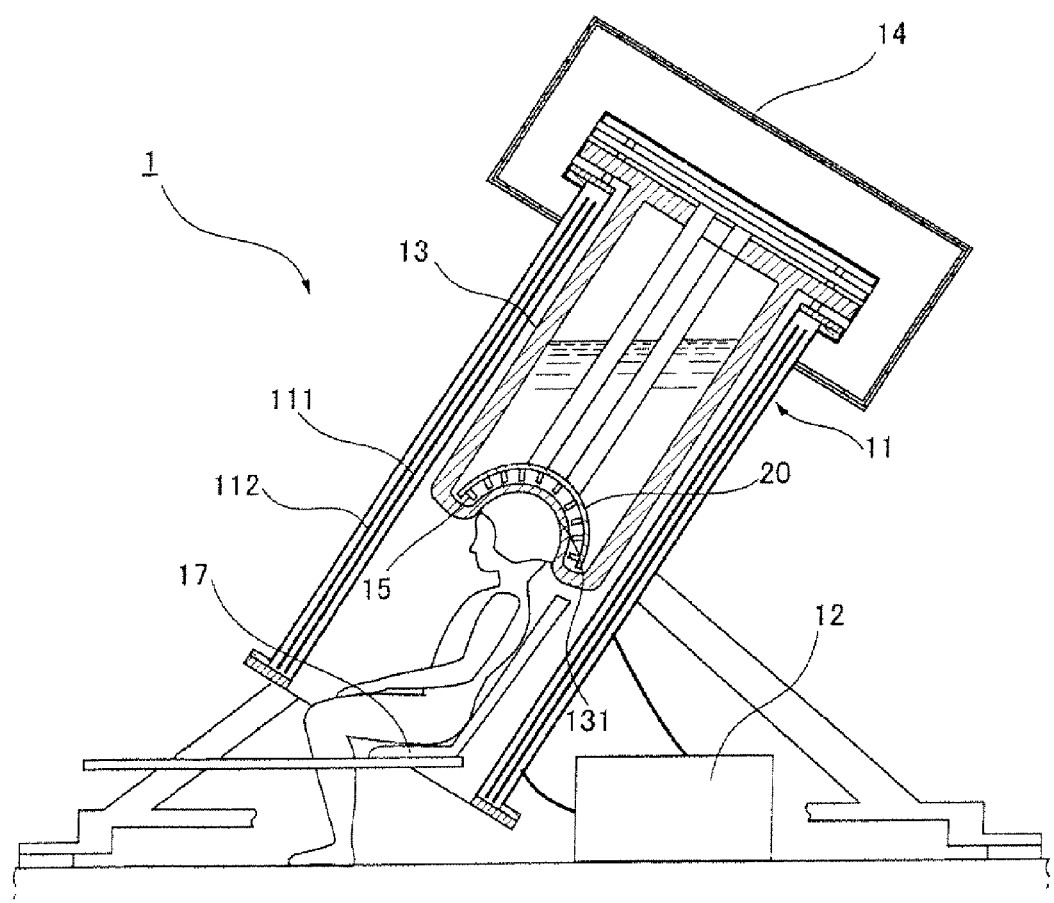
FIG. 5 illustrates diagrammatically a conventional MEG apparatus.

Referring to FIG. 1, a MEG apparatus 1 comprises a vacuum structure 11 of hollow cylinder for thermal insulation which has two cylinders—the one, inner cylinder 111 of high critical temperature superconductor material and the other, outer cylinder 112 of high-permeability magnetic material both arranged coaxially in its annular space; a closed-cycle Helium refrigerator 12 to circulate a cooled Helium gas in the pipe welded to the outside of the inner cylinder 111 in the vacuum structure 11 for thermal insulation; an liquid-Helium dewar 13 fixedly arranged in the vacuum structure 11 for thermal insulation; and a top cover 14 put on the top of the vacuum structure 11 for thermal insulation, as already described above and shown in FIG. 5.

The lower part of the liquid-Helium dewar 13 defines a head accommodating area 131 to accommodate the head of a patient (the subject under inspection). As seen in the drawing, the liquid-Helium dewar 13 has a plurality of SQUID magnetic sensors 15 therein. The magnetic sensors 15 are fixedly arranged around the head accommodating area 131. A superconducting canopy 132 is arranged above the magnetic sensors 15 in the liquid-Helium dewar 13, which is filled with liquid Helium. The superconducting canopy 132 is made of lead, $MgB_2$ or BSCCO.

The fastening means to prevent the magnetic sensors 15 from moving relative to the first cylinder 111 of high critical temperature superconductor material comprises a first pillow structure 22 to fill the gap between the inner wall of the vacuum structure 11 for thermal insulation and the outer wall of the liquid-Helium dewar 13, and a second pillow structure 21 to fill the gap between the superconducting canopy 132 and the inner wall of the liquid-Helium dewar 13. The second pillow structure 21 is placed next to the lowest end of the liquid-Helium dewar 13. One example of the first pillow structure 22 comprises a pillow 22 and two rails (not shown) laid on the inner wall of the vacuum structure 11 for thermal insulation, so that the pillow 22 can run on the parallel rails with the liquid-Helium dewar 13 laid on when it is pulled up toward the top of the vacuum structure 11 for thermal insulation.

Figure 2:
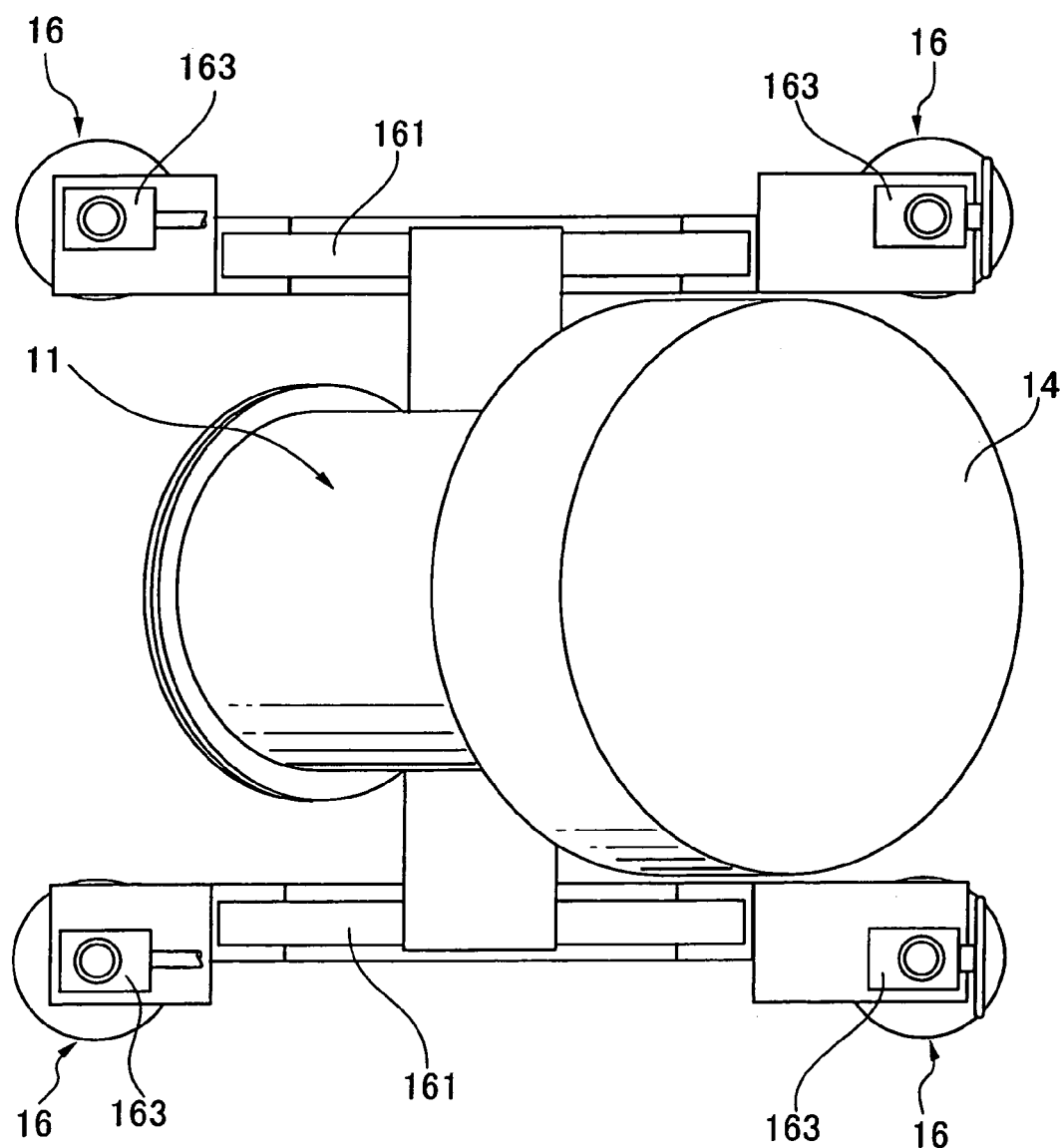
FIG. 2 is a plane view of the MEG apparatus according to the embodiment of the present invention.

The vacuum structure 11 for thermal insulation is set on the floor via four mechanical vibration-suppressor supports 16 (see FIG. 2), each comprising a mechanical vibration-absorber 161 for absorbing any mechanical vibrations from the surface of the floor and an anti-mechanical vibration mechanism 162 sensitive to any mechanical vibrations from the surface of the floor for performing feed-back control and canceling the adverse effect on the vacuum structure 11 for thermal insulation. The mechanical vibration-absorber uses rubber or air suspension.

Also, the mechanical vibration-suppressor support 16 includes an up-and-down mechanism 163, which can be conveniently removed when the MEG apparatus (1 ton in weight) is transported.

The top cover 14 is put on the top of the vacuum structure 11 for thermal insulation to effectively prevent invasion of the geomagnetism and the electromagnetic waves from the top. A significant amount of geomagnetic field still invades into the inner space of the vacuum structure 11 for thermal insulation after passing through the top cover 14. A superconducting canopy 132 is placed to protect the SQUID magnetic sensors 15 against the geomagnetic flux which the top cover 14 leaks. In this particular embodiment, the sensor support block 20 has a helmet-like shape to enclose the head of a patient under inspection. The helmet-like shape helps the support block 20 effectively shut off the magnetic field component transverse the axis of the cylinder.

The first pillow structure 22 fills the gap between the inner wall of the vacuum structure 11 for thermal insulation and the outer wall of the liquid-Helium dewar 13, while the second pillow structure 21 fills the gap between the superconducting canopy 132 and the inner wall of the liquid-Helium dewar 13. These pillows 21 and 22 help the liquid-Helium dewar 13 lie stably on the vacuum structure 11 for thermal insulation, thereby preventing any relative displacement between the SQUID magnetic sensors 15 and the first cylinder 111 of high critical temperature superconductor in the vacuum structure 11 for thermal insulation. Thus, even though the least magnitude of mechanical vibration from the floor comes to the MEG apparatus 1, it is assured that the SQUID magnetic sensors 15 and the vacuum structure 11 for thermal insulation (particularly the first cylinder 111) undergo same mechanical vibration (displacement), keeping the static magnetic field in the inner space of the vacuum structure 11 for thermal insulation unchanged relative to the SQUID magnetic sensors 15, and hence causing no noise signals to appear in the magnetic sensors.

The MEG apparatus can be put in operation as follows: First, both of the top and the bottom openings of the vacuum structure 11 for thermal insulation are closed with a magnetic member to prevent invasion of the geomagnetism in the inner space of the vacuum structure 11 for thermal insulation. Then, the first cylinder 111 is cooled down to around the liquid nitrogen temperature (below the superconducting critical temperature, 100 K) by the closed-cycle Helium refrigerator 12, thereby shutting out the surrounding magnetic field. Thus, the SQUID magnetic sensors 15 are guaranteed to be free from being inoperative because of seizures of magnetic flux. The liquid-Helium dewar 13 is filled with liquid helium, letting the SQUID magnetic sensors measure the neuro-magnetic field. As an alternative of the filling of liquid helium the liquid-Helium dewar can be cooled below the superconducting critical temperature by means of thermal conduction.

INDUSTRIAL USABILITY

Figure 3:
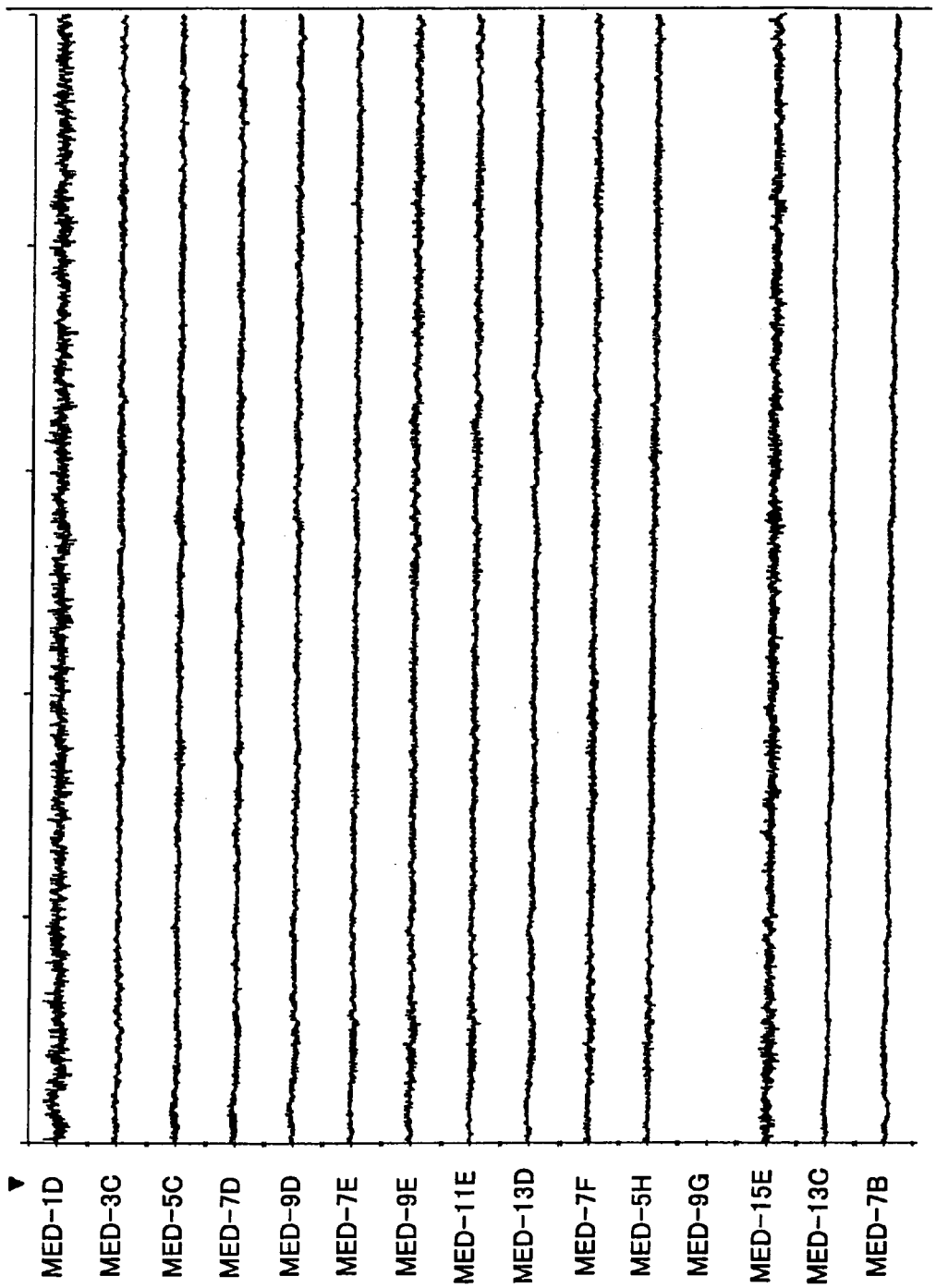
FIG. 3 shows graphic representations of noise signals appearing in the MEG apparatus according to the present invention.
Figure 4:
FIG. 4 is a graphic pattern of the neuro-magnetic field measured by the MEG apparatus according to the present invention.
Figure 6:
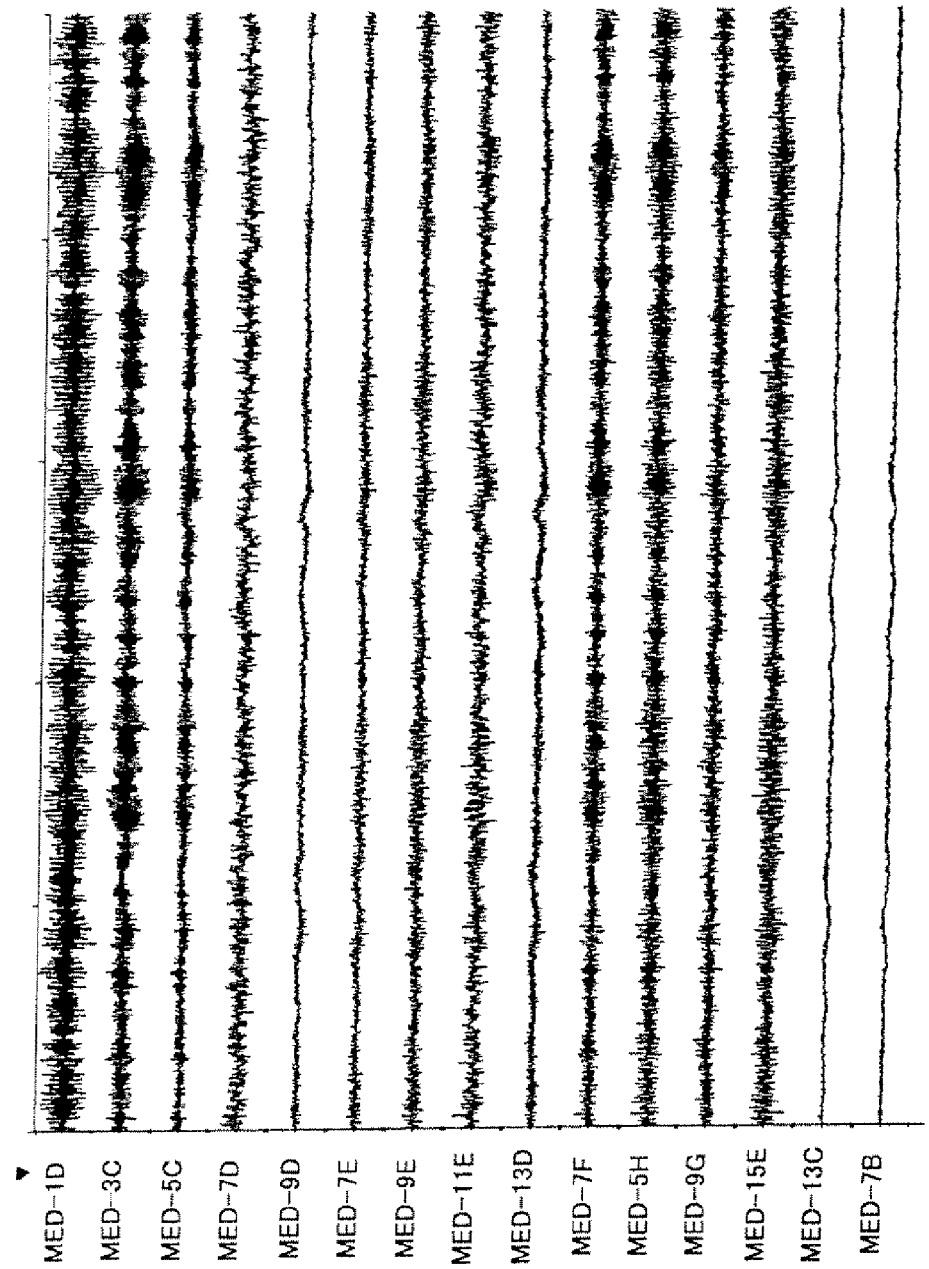
FIG. 6 shows a graph of noise signals appearing in the conventional MEG apparatus.
Figure 7:
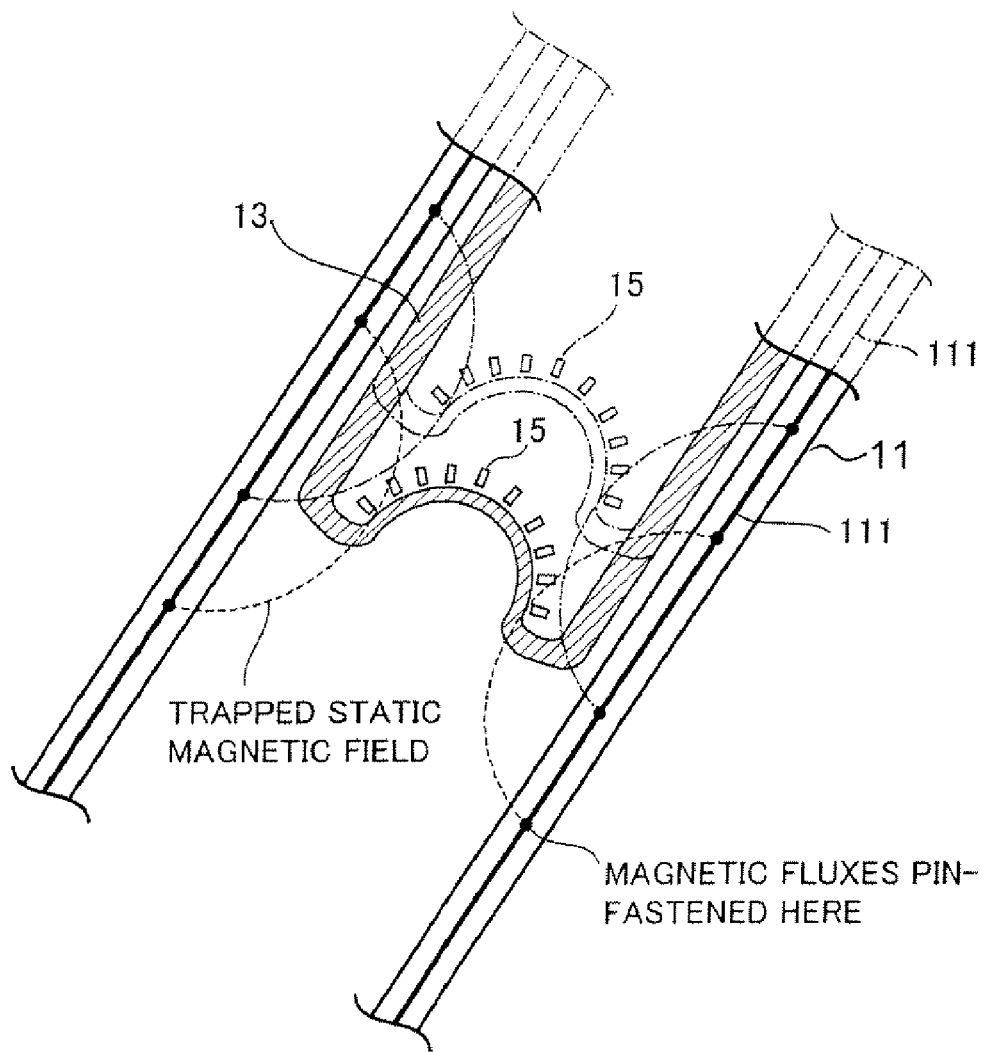
FIG. 7 illustrates the positional relation of the magnetic sensors and high critical temperature superconductor shield relative to the static geomagnetic field before and after their longitudinal displacement.
Figure 8:
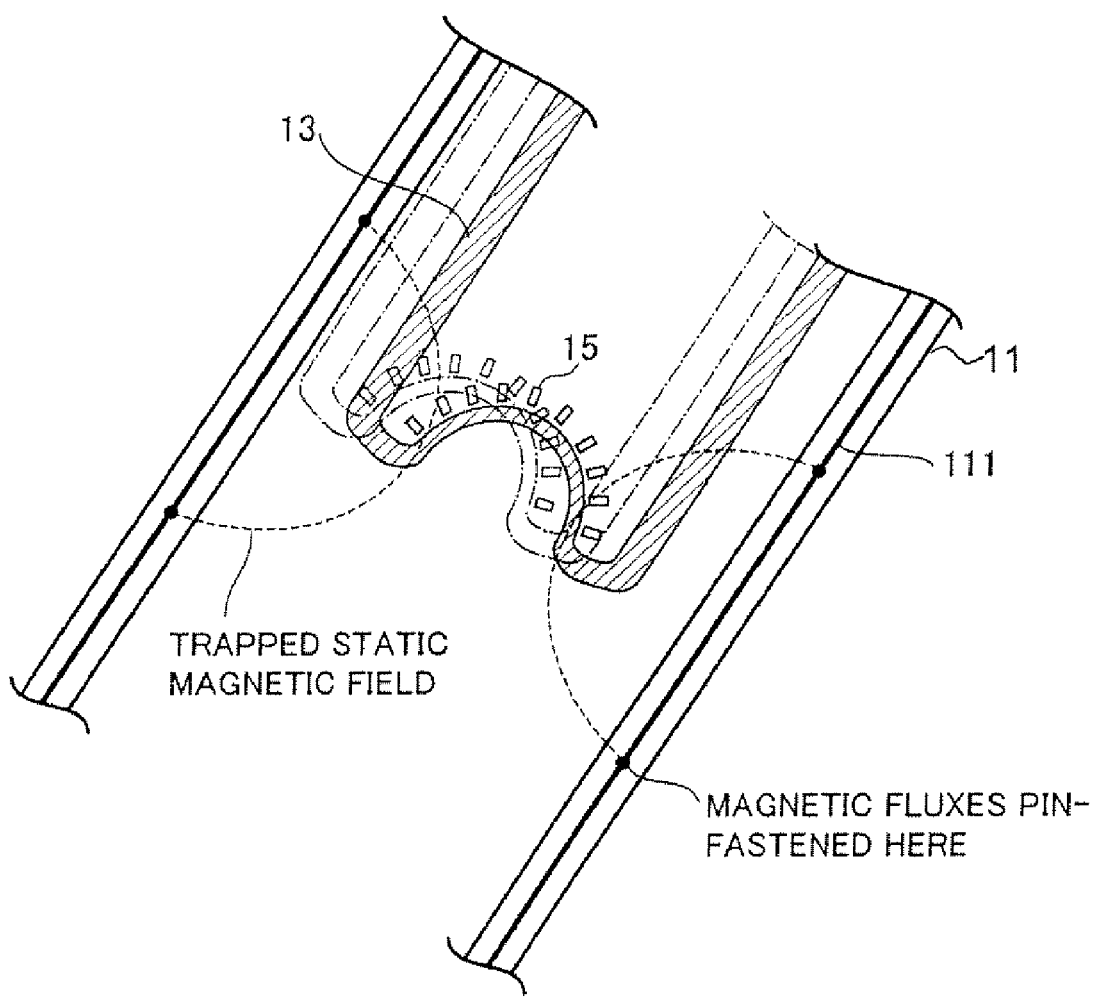
FIG. 8 illustrates the positional relation of the magnetic sensors and high critical temperature superconductor shield relative to the static geomagnetic field before and after their lateral displacement.

FIG. 3 shows graphic representation of records of noise signals from the magnetic sensors 15 in a MEG apparatus according to the present invention, the noise signals being plotted versus time (abscissa). Comparison with the noise records of FIG. 6 reveals drastic reduction of noise signals in measurement of neuro-magnetic field by the apparatus of the present invention. FIG. 4 shows the magnetic field pattern in the brain, which was drawn by plotting data from 128 magnetic sensors 15 (the strength of magnetic field given in tone.) This permits visual observation of the function and activities of the human brain under inspection on real time.

What is claimed:

1. A magnetoencephalography apparatus comprising:
a hollow, vacuum structure for thermal insulation which has two cylinders—the first cylinder of high critical temperature superconductor material and the second cylinder of high permeability magnetic material both contained therein;
a closed-cycle coolant refrigerator to circulate a given coolant in a pipe welded to the outside wall of the first cylinder in the vacuum structure for thermal insulation;
a coolant dewar fixedly arranged in the vacuum structure for thermal insulation;
a plurality of SQUID magnetic sensors fixedly arranged in the coolant dewar;
a top cover of a magnetic material to cover the top of the vacuum structure for thermal insulation, said SQUID magnetic sensors being arranged in the coolant dewar around a head-accommodating area, which is defined at the lower part of the coolant dewar; and a superconducting canopy arranged above the magnetic sensors in the coolant dewar, characterized in that the apparatus further comprises fastening means for preventing any relative displacement between the magnetic sensors and the first cylinder of high critical temperature superconductor material, the fastening means to assure that the magnetic sensors be prevented from traversing across stationary magnetic fluxes trapped in the inner space of the vacuum structure for thermal insulation, the fastening means comprising a first pillow structure to fill a gap between the inner wall of the vacuum structure for thermal insulation and the outer wall of the coolant dewar, the fastening means further comprising a second pillow structure to fill a gap between the superconducting canopy and the inner wall of the coolant dewar, the second pillow structure being placed next to the lowest end of the coolant dewar.

2. A method of operating a magnetoencephalography apparatus comprising a hollow, vacuum structure for thermal insulation which has two cylinders—the first cylinder of high critical temperature superconductor material and the second cylinder of high permeability magnetic material both contained therein, a closed-cycle coolant refrigerator to circulate a given coolant in a pipe welded to the outside wall of the first cylinder in the vacuum structure for thermal insulation, a coolant dewar fixedly arranged in the vacuum structure for thermal insulation; a plurality of SQUID magnetic sensors fixedly arranged in the coolant dewar, and a top cover of a magnetic material to cover the top of the vacuum structure for thermal insulation, a superconducting canopy arranged above the magnetic sensors in the coolant dewar, and fastening means to prevent relative displacement between the magnetic sensors and the first cylinder of high critical temperature superconductor material, and to assure that the magnetic sensors be prevented from traversing across stationary magnetic fluxes trapped in the inner space of the vacuum structure for thermal insulation, the fastening means comprising a first pillow structure to fill a gap between the inner wall of the vacuum structure for thermal insulation and the outer wall of the coolant dewar, the fastening means further comprising a second pillow structure to fill a gap between the superconducting canopy and the inner wall of the coolant dewar, the second pillow structure being placed next to the lowest end of the coolant dewar, the method comprising:

closing both the top and the lower openings of the hollow vacuum structure for thermal insulation by the magnetic members;

cooling the first cylinder down to around the liquid nitrogen temperature;

cooling the coolant dewar down below the superconducting critical temperature by filling the coolant dewar with liquid Helium or by cooling the coolant dewar by means of thermal conduction; and measuring the neuro-magnetic field by the SQUID magnetic sensors arranged in the coolant dewar, wherein the first pillow structure and the second pillow structure prevent relative displacement between the magnetic sensor and the first cylinder of high critical temperature superconductor material during the measuring.

3. A magnetoencephalography apparatus according to claim 1 wherein the apparatus further comprises a mechanical vibration-suppressor support to support the vacuum structure for thermal insulation on the floor of a building, said mechanical vibration-suppressor support comprising a mechanical vibration absorber to absorb any mechanical vibration from the floor and an anti-mechanical vibration mechanism to detect and cancel the mechanical vibration by means of feedback control.

* * * * *